US00PP24210P3

(12) United States Plant Patent
Barritt

(10) Patent No.: US PP24,210 P3
(45) Date of Patent: Feb. 4, 2014

(54) APPLE TREE NAMED 'WA 38'

(50) Latin Name: *Malus domestica*
Varietal Denomination: WA 38

(75) Inventor: Bruce H. Barritt, Okanagan Centre (CA)

(73) Assignee: Washington State University Research Foundation, Pullman, WA (US)

( * ) Notice: Subject to any disclaimer, the term of this patent is extended or adjusted under 35 U.S.C. 154(b) by 93 days.

(21) Appl. No.: 13/385,545

(22) Filed: Feb. 23, 2012

(65) Prior Publication Data

US 2013/0227750 P1 Aug. 29, 2013

(51) Int. Cl.
*A01H 5/00* (2006.01)

(52) U.S. Cl.
USPC ..... Plt./161

(58) Field of Classification Search
USPC ..... Plt./161, 170
See application file for complete search history.

(56) References Cited

U.S. PATENT DOCUMENTS

PP7,197 P * 3/1990 Luby et al. ..... Plt./161

* cited by examiner

*Primary Examiner* — Howard Locker
(74) *Attorney, Agent, or Firm* — Morrison & Foerster LLP

(57) ABSTRACT

A new and distinctive variety of a *Malus domestica* apple tree, named 'WA 38' that is distinguished by its intense and nearly full color, internal indices that are different than its parents, and its long common storage life.

4 Drawing Sheets

Latin name of the genus and species of the claimed plant: Botanical/commercial classification: *Malus domestica*/apple tree.

Varietal denomination: 'WA 38'.

BACKGROUND OF THE INVENTION

The invention refers to a new plant variety of apple tree (*Malus domestica*) named 'WA 38'. This new variety is distinguished by its intense and nearly full color, internal indices that are different than its parents, and its long common storage life.

'WA 38' originated as a single seedling from a cross of the patented varieties 'Enterprise' (U.S. Plant Pat. No. 9,193) and 'Honeycrisp' (U.S. Plant Pat. No. 7,197) in Year 1. The germinated seedling was grown in a greenhouse at Wenatchee, Wash. In September of Year 2, 'WA 38' was chip budded onto 'M9' rootstock and the resulting tree was planted in the evaluation orchard at Douglas County, Wash. in the spring of Year 5. Fruit from this originally budded tree were observed in Year 7 and Year 8 and due to the unique fruit quality traits, 'WA 38' was selected and second generation trees were made by chip budding onto M9 rootstock in the fall of Year 8. Second generation trees were planted at three locations in Washington State near Chelan, Douglas County, Wash.; near East Wenatchee, Douglas County, Wash.; and near Basin City, Franklin County, Wash. A comparison of second generation trees against the originally budded tree, including trunk, branches, leaves, flowers, and fruit; showed them to be essentially the same and stable over the years checked (Years 12, 13, 14, and 15).

SUMMARY OF THE INVENTION

The 'WA 38' apple tree variety exhibits exceptionally long storage life in common storage. 'WA 38' loses little of its crispness, sugar, and acid following five months of storage, whereas that of its parents declines considerably. The appearance of 'WA 38' fruit is nearly full color and has an intensity that is unique among other apple varieties of the same season. Like both its parents (i.e., 'Enterprise' and 'Honeycrisp'), 'WA 38' is heterozygous for the ASC1 gene and homozygous for the ACO1 gene, both of which are involved in ethylene production. These genes confer low ethylene production, which in turn affects storage life. The ACS1 and ACO1 genotypes were determined using the method described in Zhu and Barrit (2008). The harvest maturity of 'WA 38' is approximately three weeks later than that of the parental variety 'Honeycrisp', and approximately three weeks earlier than that of the parental variety 'Enterprise'. Additionally, the combination of fruit appearance and internal eating qualities of the fruit of 'WA 38' is distinctly different than that of the parental varieties 'Honeycrisp' and 'Enterprise'.

DETAILED BOTANICAL DESCRIPTION

Figure 1:
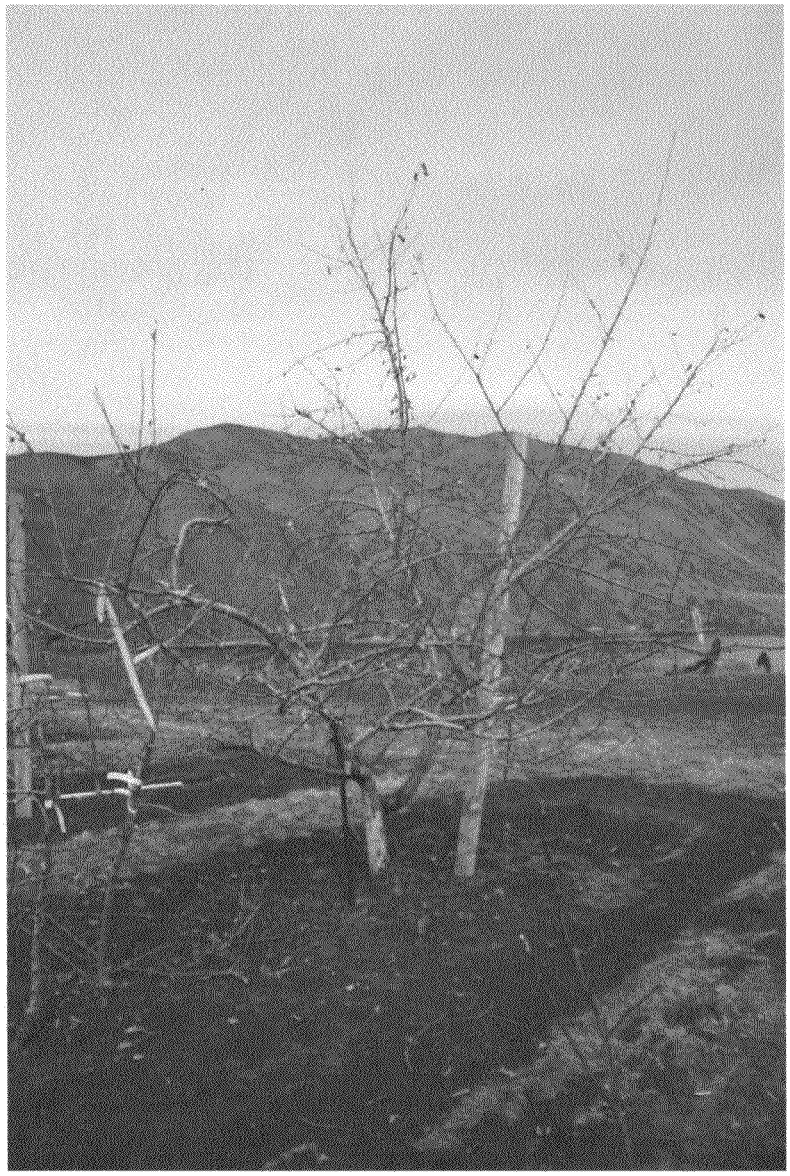
FIG. 1. View of the dormant stage of 'WA 38' originally budded tree.
Figure 2:
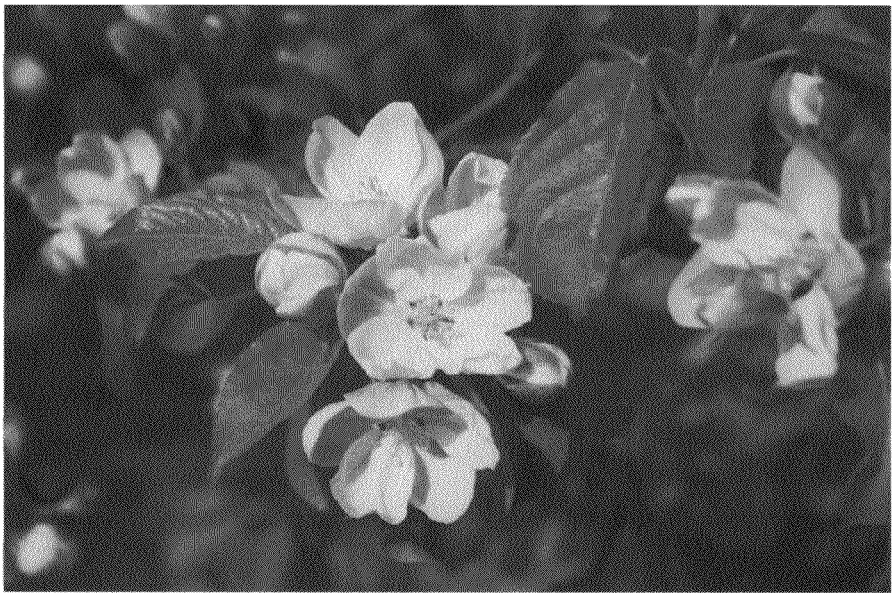
FIG. 2. View of blossoms from the originally budded tree of 'WA 38'.
Figure 3:
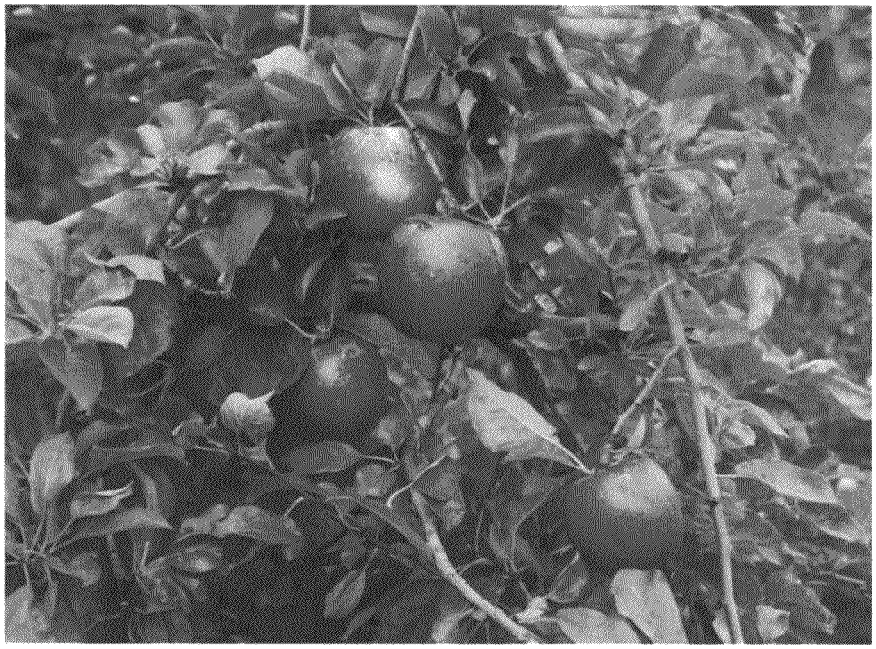
FIG. 3. View of typical 'WA 38' originally budded tree fruit at harvest maturity.
Figure 4:
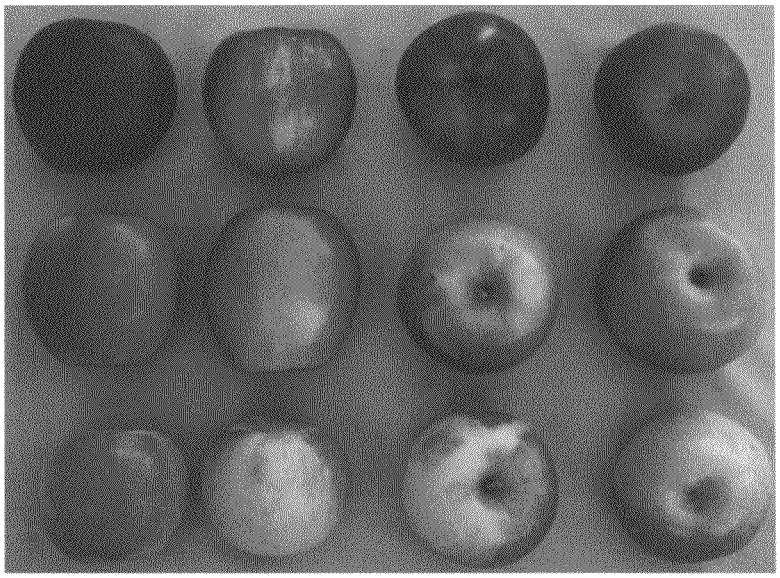
FIG. 4. View comparing harvest mature fruit of 'WA 38' (top row), and its parents 'Enterprise' (center row), and 'Honeycrisp' (bottom row).

The following detailed description, except for description of fruit, is from the 'WA 38' originally budded tree grown at Orondo, Douglas County, Wash. The 'WA 38' tree was 11 years old when measurements were taken. The USDA hardiness zone 6b. All color references are from The R.H.S. Colour Chart by The Royal Horticultural Society. The seedling was not grown on its own roots, as standard production of apple trees involves propagation on a rootstock.

Tree:

*Type.*—Spreading; moderately heavy spur development, and precocious with spur development beginning on two-year old wood.

*Vigor.*—Considered moderate on the low side with the current season's growth ranging from 26.0 cm to 50.2 cm with an average of 37.0 cm.

*Overall shape.*—Original budded tree was supported by securing the central leader to a 3-wire trellis; no branch training was performed and pruning was minimal; only branches that were likely to impact routine field operations or that were broken were removed; as such, the overall observed shape was upright and spreading with a height of 16 feet and width of 14 feet.

*Height.*—16 feet.

*Width.*—14 feet.

*Hardiness.*—Considered hardy for the regions grown in; USDA hardiness zone 6b.

*Productivity.*—Considered high.

Trunk:

*Size.*—Diameter at a height of 30 cm above graft union is 10.3 cm.

*Bark texture.*—Considered smooth for 11 year old tree.

*Bark color.*—Greyed-orange (RHS 199A).

*Lenticels.*—Present and moderate in number averaging 6 lenticels per 9 $cm^2$; shape is elongated and oriented horizontally; average width is 1.7 mm; average length is 10.9 mm.

*Lenticels color.*—Brown (RHS N200A).

Branches:

*First year branches.*—Diameter: at mid-point of growth ranges from 3.7 mm to 5.0 mm and averages 4.5 mm. Length: current season's growth ranges from 26.0 cm to 50.2 cm with an average of 37.0 cm. Bark color: greyed-orange (RHS 176A). Lenticels: numerous present, averaging 17 lenticels in a 1 cm section of branch; shape is mostly round with a few oval in shape; oriented vertically; diameter ranges from 0.4 mm to 0.9 mm; oval dimensions range from 1.4 mm to 1.6 mm in length and 0.7 mm in width; and color is green-white (RHS 157D).

*Scaffold branches.*—Size: ranges from 4.2 cm to 7.9 cm in diameter with an average of 5.9 cm as measured 10 cm from the trunk. Angle: moderately flat to near flat, ranging from 75 to 85 degrees from vertical. Branch color: grey-brown (RHS 199A). Lenticels: few in number, averaging 11 lenticels per 9 $cm^2$; shape and size is variable, mostly elongated, with some round; length ranges from 8.4 mm to 18.9 mm and width ranges from 1.0 mm to 1.7 mm; round diameter ranges from 1.0 mm to 1.3 mm; orientation is horizontal; and color is greyed-orange (RHS 166D).

Leaves:

*Shape.*—Considered broadly acute on the round side and is upward folding.

*Texture.*—Upper surface is leathery with some puckering; lower surface is smooth with some puckering.

*Sheen.*—Upper surface has a high sheen.

*Pubescence.*—Present on lower surface only covering 100% and is moderately heavy; color of lower surface pubescence is greyed-yellow (RHS 160D); light covering of white pubescence (RHS 155B) is found along veins of upper surface.

*Length.*—Blade length ranges from 7.2 cm to 8.9 cm with an average of 8.1 cm.

*Width.*—Ranges 5.2 cm to 6.3 cm with an average of 5.7 cm.

*Margin.*—Serrate with a few bi-serrate regions.

*Tip.*—Acuminate.

*Base.*—Rounded.

*Stipules.*—Present on most petioles; 0 to 2 present with most being 1; shape is acicula; length ranges from 2.0 mm to 6.3 mm with an average of 4.4 mm; width at base ranges from 1.0 mm to 1.6 mm with an average 1.3 mm; color of upper and lower surface is yellow-green (RHS 1146D); and pubescence is present on both upper and lower surfaces, considered fine with 100% coverage over both surfaces; pubescence color is greyed-yellow (RHS 160D).

*Leaf blade color.*—Upper surface is yellow-green (RHS 147A); lower surface is yellow-green (RHS 147C).

*Mid-vein.*—Prominent with considerable fine pubescence on under surface of vein; width at mid blade ranges from 1.1 mm to 1.6 mm with an average 1.4 mm; upper surface color is yellow-green (RHS 147A); lower surface color is yellow-green (RHS 147C); pubescence covering 100% of the lower surface is greyed-yellow (RHS 160D).

*Petiole.*—Length ranges from 24.5 mm to 35.9 mm with an average of 30.1 mm; shallow groove runs the entire length of the upper surface; diameter at mid point ranges from 1.4 mm to 1.9 mm with an average of 1.7 mm; color of upper surface is yellow-green (RHS 145C); color of lower surface is yellow-green (RHS 145D); pubescence is abundant and fine over the entire length and circumference of the petiole; color of pubescence is greyed-yellow (RHS 160D).

*Buds.*—Usually on single spurs; shape is considered acute with base being truncate with spur; diameter ranges from 4.1 mm to 4.9 mm with an average of 4.4 mm; length ranges from 6.6 mm to 10.2 mm with an average of 8.3 mm; bud scale color is purple (RHS N77A).

Flowers: Bloom started April 19 and finished May 6, with full bloom date May 1 at Orondo, Douglas County, Wash.; number of blossoms per bud ranges from 4 to 6 with an average of 6; fragrance is apple-blossom like.

*Size.*—Considered large, when fully expanded the diameter ranged from 51.6 mm to 57.5 mm with an average of 53.9 mm.

*Petal.*—Width ranges from 18.0 mm to 21.1 mm with an average 19.2 mm; length ranges from 24.4 mm to 27.3 mm with an average 25.2 mm; shape is elliptic; typical petal number is five; petal margins are smooth, both tip and base of petal are rounded; petal surface is slightly glabrous.

*Color.*—Both upper and lower surfaces are white (RHS 155B); where exposed prior to opening, lower surface has red-purple highlights (RHS 64B).

*Stamen.*—Number ranges from 18 to 21 with an average of 21; filament length ranges from 5.5 mm to 11.2 mm with an average of 8.5 mm; filament color is white (RHS 155C); anthers are kidney shaped with an average size of 1.6 mm wide×2.7 mm long; mature anther color is yellow (RHS 10D).

*Pistil.*—Typically five pistils per flower; length ranges from 14.7 mm to 19.7 mm with an average of 17.2 mm. Styles: five in number, fused at ⅓ distance from basal end with the fused region covered in white (RHS 155B) pubescence; color is yellow-green (RHS 145B). Stigma: round club shaped 0.6 to 0.7 mm in diameter; color is yellow-green (RHS 153B).

*Sepals.*—Five per blossom; shape is considered thin deltoid with the tip being acuminate and the base being truncate; length ranges from 13.2 mm to 8.8 mm with an average of 11.9 mm; width ranges from 3.8 mm to 4.4 mm with an average of 4.1 mm; abundant white (RHS 155B) pubescence is present on both upper and lower surfaces; upper surface color is yellow-green (RHS 146C); lower surface color is yellow-green (RHS 148D); both upper and lower tip surfaces red-purple highlight color (RHS 64B).

*Peduncle.*—Length ranges from 16.1 mm to 23.0 mm with an average of 19.5 mm; color is yellow-green (RHS 146B); considerable white downiness (RHS 155B) present over the entire surface.

*Pollen.*—Moderate amounts of pollen are produced, with yellow color (RHS 10D).

Fruit: Observations and testing from 1$^{st}$ generation tree fruit grown at East Wenatchee, Douglas County, Wash.; production is moderate to heavy, falling within the range of existing commercial cultivars.

*Form.*—Considered uniform round-conical.

*Size.*—Considered medium large with a normal crop level; equatorial diameter ranges from 80.0 mm to 88.3 mm with an average of 83.9 mm; axis diameter ranges from 76.4 mm to 85.6 mm with an average of 79.0 mm; typical weight ranges from 254 g to 332 g with an average of 281 g.

*Stem.*—Considered long and medium thick; length ranges from 22.3 mm to 29.5 mm and averages 25.7 mm; diameter ranges from 1.8 mm to 2.8 mm with an average of 2.3 mm; color is yellow-green (RHS 146B).

*Stem cavity.*—Width ranges from 28.3 mm to 36.1 mm with an average 32.6 mm; depth ranges from 20.9 mm to 23.9 mm with an average of 22.7 mm; occasional light russet over bottom ⅓ of cavity; cavity shape is acuminate; stem cavity is not lipped.

*Basin cavity.*—Considered abrupt; surface is wavy; puckered around eye; light ribbing; green-white (RHS 157D) downy hairs at base; width ranges from 25.9 mm to 31.5 mm with an average of 28.8 mm; depth ranges from 11.6 mm to 18.4 mm with an average of 13.8 mm.

*Eye.*—Erect convergent; sepal color is yellow-green (RHS 148C); sepals contain green-white (RHS 157D) downy hairs.

*Skin.*—Texture is considered tender; thickness is considered thin; appearance is considered more streaked than marbled with scant bloom present; skin color of over streak is greyed-purple (RHS 183B); skin color of under streak is greyed-purple (RHS 183D); skin under color is red (RHS 48A); skin lenticels are numerous, small, round, smooth with the skin; skin lenticels are more numerous towards the calyx end averaging 4 lenticels per cm$^2$ at stem end, 11 lenticels per cm$^2$ at calyx end; areolar at the stem end; color is white (RHS 155B) and areolar color is from the red group (RHS 48A); skin lenticel size ranges from 0.2 mm to 0.5 mm in diameter with aerolar diameter ranging from 1.0 mm to 1.5 mm.

*Core.*—Core position is considered median; core line position is basal meeting; core diameter ranges from 38.7 mm to 46.3 mm with an average of 42.9 mm; core length ranges from 28.2 mm to 32.8 mm with an average of 30.5 mm; core shape is flat conical.

*Cell (locule or carpel).*—Five per fruit; not tufted; shape is elliptical; length ranges from 17.1 mm to 23.4 mm with an average of 19.6 mm; width (axis/edge) ranges from 10.9 mm to 12.8 mm with an average of 11.6 mm; depth (wall/wall) ranges from 5.7 mm to 7.5 mm with an average of 6.5 mm.

*Tube.*—Cone shaped.

*Stamen position.*—Median relative to stamens situated approximately in the middle of the tube (the cavity just beneath the eye).

*Cell attachment to axis.*—Axial and open, meaning cells are symmetrical and each cell is open.

*Seed.*—Number ranges from 1 to 3 with an average of 2; shape is acute; seed length ranges from 8.3 mm to 9.4 mm with an average of 9.0 mm; seed width ranges from 4.0 mm to 4.7 mm with an average of 4.3 mm; seed color is brown (RHS 200D).

*Flesh.*—Crisp, melting, juicy, sub-acid with mild apple like flavor; color is yellow-white (RHS 158D); flesh browning very little to none after one hour; quality is very good.

*Aroma.*—Apple like and moderate in intensity.

*Date of harvest maturity.*—Typically late September/early October, observed harvest maturity of current season was October 2; for any one location, 'WA 38' typically can be classed as a single pick variety; however, harvest can be extended into two picks over a two week period.

*Genotype.*—WA 38 is heterozygous (1,2) for ACS1 and is homozygous (2,2) for ACO1.

*Keeping quality.*—Excellent; up to five months in common storage; flesh browns very slightly after being exposed.

Pollination: Any diploid apple of the same bloom season.

Use: For dessert.

Disease and insect resistance: May have some resistance to *Venturia inaequalis* (apple scab) from its maternal parent 'Enterprise'; otherwise is considered to be susceptible to all insects and diseases found in the region of Central Washington.

Table 1 represents maturity indices of the 'WA 38', 'Honeycrisp' and 'Enterprise' varieties. In Table 1, pressure is a measure of fruit firmness, ° Brix is a measure of soluble solid content of fruit, and titratable acid is a measure of fruit acidity. The mature harvest date of 'Enterprise' was October 23, Year 15, and the mature harvest date of 'Honeycrisp' was September 10, Year 15.

TABLE 1

Maturity indices

| Variety | Sample Run Date | Pressure (Newtons) | °Brix | pH | Titratable Acid (g/ 100 ml) |
|---|---|---|---|---|---|
| 'WA 38' | October 2, Year 15 | 82 | 12.6 | 3.47 | 0.62 |
| 'Honeycrisp' | September 10, Year 15 | 62 | 12.7 | 3.52 | 0.42 |
| 'Enterprise' | October 23, Year 15 | 86 | 14.3 | 3.47 | 0.68 |

What is claimed:

1. A new and distinct apple tree variety named 'WA 38', as herein shown and described.

* * * * *

'WA 38'

'Enterprise'

'Honeycrisp'